(12) United States Patent     (10) Patent No.:    US 8,348,904 B2
Petersen     (45) Date of Patent:    Jan. 8, 2013

(54) MEDICAL DELIVERY SYSTEM HAVING CONTAINER RECOGNITION AND CONTAINER FOR USE WITH THE MEDICAL DELIVERY SYSTEM

(75) Inventor: Jan L. Petersen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 511 days.

(21) Appl. No.: 12/532,004

(22) PCT Filed: Mar. 14, 2008

(86) PCT No.: PCT/EP2008/053131
§ 371 (c)(1),
(2), (4) Date: Nov. 19, 2009

(87) PCT Pub. No.: WO2008/113772
PCT Pub. Date: Sep. 25, 2008

(65) Prior Publication Data
US 2010/0106100 A1    Apr. 29, 2010

Related U.S. Application Data

(60) Provisional application No. 60/920,097, filed on Mar. 26, 2007.

(30) Foreign Application Priority Data

Mar. 21, 2007   (EP) .................................... 07104555

(51) Int. Cl.
*A61M 5/00*     (2006.01)
(52) U.S. Cl. ....................................... 604/207
(58) Field of Classification Search .................. 604/207, 604/208, 187, 232
See application file for complete search history.

(56) References Cited

U.S. PATENT DOCUMENTS

| | | |
|---|---|---|
| 3,700,862 A | 10/1972 | Snook et al. |
| 3,809,863 A | 5/1974 | Oberg |
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Heyman et al. |

(Continued)

FOREIGN PATENT DOCUMENTS

CN     1013704     8/1991

(Continued)

OTHER PUBLICATIONS

International Search Report for PCT/EP07/054069, mailed Sep. 17, 2007.

(Continued)

*Primary Examiner* — Kevin C Sirmons
*Assistant Examiner* — Deanna K Hall
(74) *Attorney, Agent, or Firm* — Wesley A. Nicolas; Marc A. Began; Reza Green

(57) ABSTRACT

A medical delivery system comprising a container and a dosing assembly where the container is fastenable to the dosing assembly. When the container is secured to the dosing assembly, a recognition feature on the container is adapted to co-operate with a variable resistor disposed in the dosing assembly to thereby facilitate an identification of the specific type of container which is secured to the dosing assembly. Furthermore, the present invention relates to a container and a dosing assembly suitable for use in the medical delivery system according to the present invention.

26 Claims, 6 Drawing Sheets

U.S. PATENT DOCUMENTS

| | | |
|---|---|---|
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyot et al. |
| 5,153,827 A | 10/1992 | Coutre et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | Colgate et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,792,117 A | 8/1998 | Brown |
| 5,793,502 A | 8/1998 | Bianco et al. |
| 5,821,521 A | 10/1998 | Bridgelall et al. |
| 5,821,524 A | 10/1998 | Horlbeck et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,743,202 B2 * | 6/2004 | Hirschman et al. ........... 604/131 |
| 6,813,868 B2 | 11/2004 | Baldwin et al. |
| 6,854,653 B2 | 2/2005 | Eilersen |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2003/0015590 A1 | 1/2003 | Chen |
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1 | 10/2004 | Atterbury et al. |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0176267 A1 | 8/2006 | Honeyman et al. |
| 2006/0226238 A1 | 10/2006 | Salib et al. |
| 2006/0243804 A1 | 11/2006 | Christoffersen et al. |
| 2007/0080234 A1 | 4/2007 | Domoy |
| 2008/0015510 A1 | 1/2008 | Sandoz et al. |
| 2009/0088701 A1 | 4/2009 | Larsen |

FOREIGN PATENT DOCUMENTS

| | | |
|---|---|---|
| CN | 1051152 | 9/1993 |
| DE | 2636634 | 2/1978 |
| DE | 3712089 | 10/1988 |
| DE | 4234016 | 4/1993 |
| DE | 4402319 | 8/1994 |
| DE | 19504111 | 8/1995 |
| DE | 19637967 | 10/1997 |
| DE | 19814687 | 2/1999 |
| DE | 10035192 | 10/2001 |
| EP | 235691 | 9/1987 |
| EP | 248165 | 12/1987 |
| EP | 336778 | 10/1989 |
| EP | 364010 | 4/1990 |
| EP | 398717 | 11/1990 |
| EP | 402553 | 12/1990 |
| EP | 492954 | 7/1992 |
| EP | 573129 | 12/1993 |
| EP | 588427 | 3/1994 |
| EP | 626660 | 11/1994 |
| EP | 685810 | 12/1995 |
| EP | 690457 | 1/1996 |
| EP | 716290 | 6/1996 |
| EP | 833273 | 4/1998 |
| EP | 833278 | 4/1998 |
| EP | 911859 | 4/1999 |
| EP | 1142643 | 10/2001 |
| EP | 1143643 | 10/2001 |
| EP | 1193641 | 4/2002 |
| EP | 1246127 | 10/2002 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 59-131917 A | 7/1984 |
| JP | 63-100303 A | 5/1988 |
| JP | 2-85370 A | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5-500917 | 2/1993 |
| JP | 5-314296 | 11/1993 |
| JP | 6-163027 | 6/1994 |
| JP | 6-333102 | 12/1994 |
| JP | 7-098752 | 4/1995 |
| JP | 7-271890 | 10/1995 |
| JP | 8-106648 | 4/1996 |
| JP | 8-118864 | 5/1996 |
| JP | 8-179475 | 7/1996 |
| JP | 8-220994 | 8/1996 |
| JP | 8-262980 | 10/1996 |
| JP | 9-16703 | 1/1997 |
| JP | 9-034361 | 2/1997 |
| JP | 9-091364 | 4/1997 |
| JP | 9-192220 | 7/1997 |
| JP | 9-223181 | 8/1997 |
| JP | 9-274637 | 10/1997 |
| JP | 10-105635 | 4/1998 |
| JP | 10-268777 | 10/1998 |
| JP | 11-135172 | 5/1999 |
| JP | 11-162591 | 6/1999 |
| JP | 11-180079 | 7/1999 |
| JP | 11-316877 | 11/1999 |
| JP | 2000-040119 | 2/2000 |
| JP | 2000-272191 | 10/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | WO 95/24317 | 9/1995 |
| WO | WO 95/28190 | 10/1995 |
| WO | WO 99/60533 | 11/1999 |
| WO | WO 99/65548 | 12/1999 |
| WO | WO 00/42678 | 7/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | WO 02/11792 | 2/2002 |
| WO | WO 02/13133 | 2/2002 |
| WO | WO 02/092153 | 11/2002 |
| WO | WO 02/095675 | 11/2002 |
| WO | WO 03/017915 | 3/2003 |
| WO | WO 03/020598 | 3/2003 |
| WO | WO 03/038738 | 5/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | WO 2007/039148 | 4/2007 |
| WO | WO 2007/107562 | 9/2007 |
| WO | WO 2007/116090 | 10/2007 |
| WO | WO 2007/122253 | 11/2007 |
| WO | WO 2009/015933 | 2/2009 |

OTHER PUBLICATIONS

International Search Report for PCT/EP07/053558, mailed Jul. 23, 2007.
International Search Report for PCT/EP06/009240, mailed Jan. 4, 2007.
CN 1051152 English Abstract, Sep. 15, 1993.
CN 1013704 English Abstract, Aug. 28, 1991.
DE 19814687 Machine Translation, Feb. 18, 1999.
DE 19637967 English Abstract, Oct. 30, 1997.
DE 19504111 Machine Translation, Aug. 10, 1995.
DE 10035192 Machine Translation, Oct. 11, 2001.
DE 4402319 English Abstract, published Aug. 4, 1994.
DE 4234016 English Abstract, Apr. 15, 1993.
DE 3712089 English Abstract, Oct. 27, 1988.
DE 2636634 English Abstract, Feb. 16, 1978.
FR 2771111 Machine Translation, May 21, 1999.
JP 2002-517737 Machine Translation, Jun. 18, 2002.
JP 2002-082120 English Abstract, Mar. 22, 2002.
JP 2001-075480 English Abstract, Mar. 23, 2001.
JP 2001-043301 Machine Translation, Feb. 16, 2001.
JP 2000-040119 Machine Translation, Feb. 8, 2000.
JP 2000-272191 Machine Translation, Oct. 3, 2000.
JP 11-316877 Machine Translation, Nov. 16, 1999.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-274637 Machine Translation, Oct. 21, 1997.
JP 9-223181 Machine Translation, Aug. 26, 1997.
JP 9-192220 Machine Translation, Jul. 29, 1997.
JP 9-091364 Machine Translation, Apr. 4, 1997.
JP 9-034361 Machine Translation, Feb. 7, 1997.
JP 9-16703 Machine Translation, Jan. 17, 1997.
JP 8-262980 Machine Translation, Oct. 11, 1996.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-271890 Machine Translation, Oct. 20, 1995.
JP 7-098752 Machine Translation, Apr. 11, 1995.
JP 6-333102 Machine Translation, Dec. 2, 1994.
JP 63-100303A English Abstract, May 2, 1988.
JP 6-163027 Machine Translation, Jun. 10, 1994.

JP 59-131917 English Abstract, Jul. 28, 1984.
JP 5-314296 Machine Translation, Nov. 26, 1993.
JP 5-500917 English Abstract, Feb. 25, 1993.
JP 4-233684A English Abstract, Aug. 21, 1992.
JP 4-233680A English Abstract, Aug. 21, 1992.
JP 4-233624B2 Machine Translation, Dec. 19, 2008.
JP 4-222084 English Abstract, Aug. 12, 1992.
JP 3-27037A English Abstract, Feb. 5, 1991.
JP 2-250083 English Abstract, Oct. 5, 1990.
JP 2-188702 English Abstract, Jul. 24, 1990.
JP 2-85370 English Abstract, Mar. 26, 1990.
WO 01/22348 English Abstract, Mar. 29, 2001.
Non-Final Office Action mailed Jan. 4, 2008 in U.S. Appl. No. 11/396,889, filed Apr. 3, 2006 by Christoffersen et al.
Notice of Allowance mailed Sep. 17, 2009 in U.S. Appl. No. 11/296,991, filed Dec. 8, 2005 by Eilersen et al.
Notice of Allowance mailed Apr. 30, 2009 in U.S. Appl. No. 11/296,991, filed Dec. 8, 2005 by Eilersen et al.
Non-Final Office Action mailed Oct. 14, 2008 in U.S. Appl. No. 11/296,991, filed Dec. 8, 2005 by Eilersen et al.
Corrected Notice of Allowance mailed Jun. 19, 2009 in U.S. Appl. No. 11/232,469, filed Sep. 19, 2005 by Christoffersen et al.
Notice of Allowance mailed Jun. 8, 2009 in U.S. Appl. No. 11/232,469, filed Sep. 19, 2005 by Christoffersen et al.
Non-Final Office Action mailed Dec. 17, 2008 in U.S. Appl. No. 11/232,469, filed Sep. 19, 2005 by Christoffersen et al.
Final Office Action mailed Jul. 2, 2008 in U.S. Appl. No. 11/232,469, filed Sep. 19, 2005 by Christoffersen et al.
Non-Final Office Action mailed Jan. 3, 2008 in U.S. Appl. No. 11/232,469, filed Sep. 19, 2005 by Christoffersen et al.
Non-Final Office Action mailed Jun. 19, 2007 in U.S. Appl. No. 11/232,469, filed Sep. 19, 2005 by Christoffersen et al.
Non-Final Office Action mailed Oct. 23, 2003 in U.S. Appl. No. 10/463,915, filed Jun. 18, 2003 by Eilersen et al.
Non-Final Office Action mailed Apr. 15, 2004 in U.S. Appl. No. 10/463,915, filed Jun. 18, 2003 by Eilersen et al.
Notice of Allowance mailed Aug. 16, 2004 in U.S. Appl. No. 10/463,915, filed Jun. 18, 2003 by Eilersen et al.
Notice of Allowance mailed Aug. 13, 2003 in U.S. Appl. No. 09/925,995, filed Aug. 9, 2001 by Eilersen et al.
Non-Final Office Action mailed Nov. 12, 2002 in U.S. Appl. No. 09/925,995, filed Aug. 9, 2001 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.
Notice of Allowance mailed Oct. 8, 2002 in U.S. Appl. No. 09/846,799, filed May 1, 2001 by Aasmul et al.
Non-Final Office Action mailed May 8, 2002 in U.S. Appl. No. 09/846,799, filed May 1, 2001 by Aasmul et al.

* cited by examiner

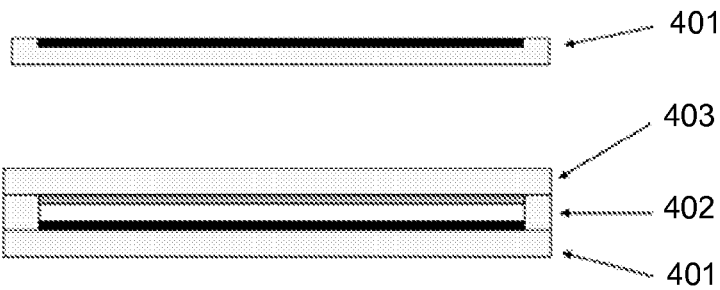
Fig. 9a
Fig. 9b
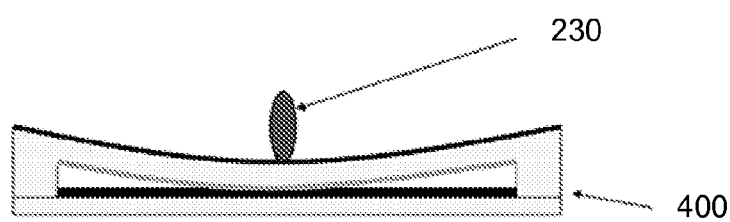
Fig. 9c
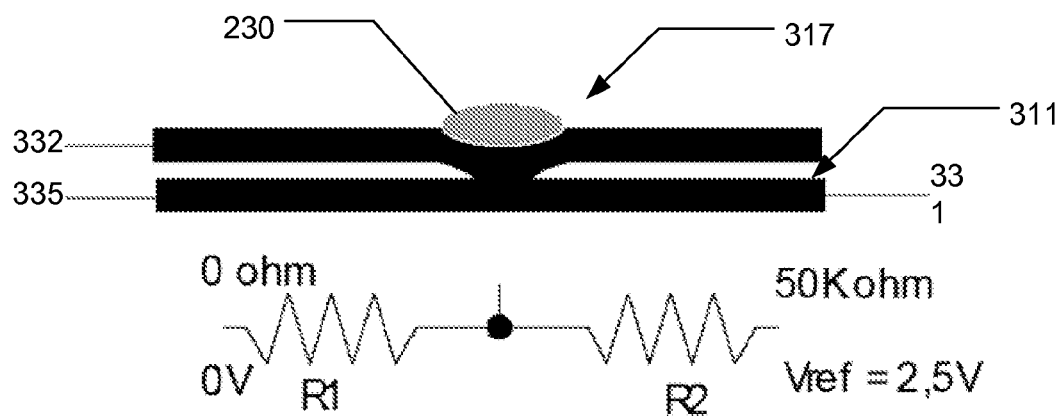
Fig. 10

MEDICAL DELIVERY SYSTEM HAVING CONTAINER RECOGNITION AND CONTAINER FOR USE WITH THE MEDICAL DELIVERY SYSTEM

CROSS-REFERENCE TO RELATED APPLICATIONS

This application is a 35 U.S.C. §371 national stage application of International Patent Application PCT/EP2008/053131 (published as WO 2008/113772), filed Mar. 14, 2008, which claimed priority of European Patent Application 07104555.3, filed Mar. 21, 2007; this application further claims priority under 35 U.S.C. §119 of U.S. Provisional Application No. 60/920,097, filed Mar. 26, 2007.

FIELD OF THE INVENTION

The present invention relates to a medical delivery system comprising a container and a dosing assembly. In particular the present invention relates to a medical delivery system wherein the dosing assembly comprises a variable resistor configured for coupling with a recognition feature of a container for providing recognition of the particular container which is secured to the dosing assembly. Furthermore, the present invention relates to a container and a dosing assembly each of which are suitable for use in the medical delivery system according to the present invention.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container and the associated delivery system to the needs of particular users. Variation of container volume may be provided by changing the length or diameter of the container. These modifications usually imply corresponding modifications of the dosing assembly of a medication delivery system so as to provide a particular stroke of a driving element for expelling the medicament from the container or to provide optimal dosing precision. Further discrimination between different medicament containers may be occasioned by the design requirements for each particular delivery system, such as required sliding friction of a piston accommodated in the container etc.

In order to discriminate between a larger variety of available containers, numerous container coding systems have been developed which primarily relies on the electronic reading and recognition of specific distinct containers in order to exclusively allow delivery of a specific type of a medicament by a dedicated delivery device. The following coding systems are known in the art:

US 2004/0178255 discloses an administering system where an ampoule having at least two recognition elements can be recognized by at least two associated sensors located at predetermined positions in the administering apparatus. Alternatively, the at least two recognition elements of the ampoule are detected by at least one sensor which can be moved, for example, by means of motor, past the recognition elements, to detect the relative position of the recognition elements.

U.S. Pat. No. 7,104,973 and WO 2005/075010 both relates to medical delivery systems wherein an ampoule having one or more mechanical surface structures is configured to activate switch elements of an associated administering apparatus in order to facilitate recognition of the ampoule. Both of these systems require that a particular dosing assembly is designed for the particular container associated with the dosing assembly. For a particular container carrying a specific code which is selected from a number of different possible codes, the sensor position of the dosing assembly has to be selected in accordance with that particular container. Alternatively, the dosing assembly requires a large number of sensors in order to facilitate sensing of different codes.

BRIEF DESCRIPTION OF THE INVENTION

Having regard to the above-identified prior art devices, it is an object of the present invention to provide an alternative to the known systems. Furthermore, it is an object of the present invention to provide a medication delivery system wherein the elements required for coding a container and for recognizing the coding of the container are minimized so that the coding elements and the sensor circuitry only occupies a small amount of space. Furthermore, it is an object of the present invention to provide a simple and cost effective coding system, wherein a large number of distinct codes can be recognized with a limited number of sensors.

In a first aspect the present invention relates to a medical delivery system comprising:
a container adapted to contain a medicament in a reservoir and to contain a slideably arranged piston which is moveable along a first axis in a distal direction towards an outlet of the reservoir so as to reduce the volume of the reservoir and expel the medicament through the outlet, the container further comprising a first mechanical feature, the location of the first mechanical feature representing at least one parameter associated with the container,
a dosing assembly adapted to be secured to the container so as to allow driving means of the dosing assembly to move the piston of the container in the distal direction, the dosing assembly further having electric circuitry configured for identifying the location of said first mechanical feature on the container,
wherein the medical delivery system comprises a first electric resistive track disposed in the dosing assembly, and a first wiper slideably engaging said first electric resistive track, the first wiper being associated with said first mechanical feature when the container is secured to the dosing assembly, the first resistor track and the first wiper being coupled to the electric circuitry and the electric circuitry being configured to detect the relative position of the first wiper with respect to the first electric resistive track, thereby enabling identification of the container when the container is secured to the dosing assembly.

Generally, as the electric resistive track in some embodiments forms a continuous track providing a reading along an analog scale, the position of the distinct coding features can be selected from a large number of discrete positions, and thus a coding system having a large number of distinct codings is obtained.

The container may be of the kind having a cylindrical wall section and wherein a slideably arranged piston is arranged to be moved along the central axis of the container.

The mechanical feature may be provided by a distinct element, such as a protrusion which is formed in a wall section of the container. Alternatively the distinct element is provided as a depression. The location of the protrusion is selected from a range of predefined locations where each location represents one or more specific parameters of the container, i.e. information relating to mechanical aspects of the container, and/or information relating to the medicament to be contained in the container. Information relating to the medicament may comprise data regarding type or kind of the medicament, the concentration, etc.

The dosing assembly may comprise a first switch element which is adapted to cooperate with a second protrusion disposed on the container so that the first switch element may be used for signaling that a container is fully seated in or on the dosing assembly, i.e. ready for reading the position of the first protrusion.

In addition, or alternatively, the dosing assembly may comprise a second switch element which is also adapted to cooperate with said second protrusion disposed on the container. The second switch element is preferably adapted to activate a controller of the electric circuitry when a container is initially pressed axially against the dosing assembly. In this way the monitoring of the container coupling is initiated. Particularly, when the fastening design of the medical delivery system is configured for requiring an initial axial movement followed by a rotational locking motion, then the second switch element may be tripped when the initial axial movement is initiated.

In another embodiment, the medical delivery system comprises two electric resistive tracks disposed in the dosing assembly, and first and second wipers configured for slideably engaging each electric resistive track. In such an embodiment, both electric resistive tracks are adapted to co-operate with respective wipers, and each wiper may be associated with a corresponding protrusion on a container when the container is fastened to the dosing assembly. Such a system may be configured for redundantly reading two identical container features provided on a single container to thereby increase container recognition reliability.

Alternatively, the two electric resistive tracks may be used con-jointly to increase the number of distinct system codings when using two respective protrusions on the container where the combination of orientation of the two protrusions is indicative of the type of container. As a further alternative, in a system where the container can be selectively fastened in two different orientations with respect to the dosing assembly, the two resistive tracks may be used to ensure that the position of a single protrusion of a container is readable irrespective of the particular selective orientation of the container.

In further embodiments, the container has a proximal end adapted to be at least partly received in the dosing assembly. When at least one of the protrusions of the container is located at the proximal end of the container and extends in the proximal direction, the force exerted for pulling the container towards the dosing assembly may be used to provide a well defined force for the protrusions to engage the one or more electric resistive tracks and the one or more switch elements.

Alternatively, or in addition, protrusions may be arranged on an external or internal face of a cylindrical section of the container. In embodiments where the proximal end of the container is adapted to be inserted into a cavity of the dosing assembly, the resistive tracks and switch elements may be arranged on a corresponding internal surface of a cylindrical cavity of the dosing assembly.

The electric resistive track may be arranged in a plane perpendicular to the longitudinal axis of the container i.e. normal to the direction of the movement of the piston when the piston is driven towards the distal end. This provides a particular space-saving construction where all movements for encoding the container information is carried out in a single plane which is typically arranged at the interface between the container and the dosing assembly.

The electric resistive track of the dosing assembly may be formed as a thin film potentiometer or a thick film potentiometer. A thin film potentiometer may comprise a first layer comprising a conductive resistive track and a second layer comprising a silver conductive layer having a low resistance. When not being manipulated by external forces, the two layers are kept apart by a spacer layer along the conductive resistive track, so that in the rest position, no galvanic contact is obtained between the two layers. Local contact between the two layers may be provided by pressing a point-like member against the external face of one of the two layers so that a wiper is formed.

In some embodiments the wiper of the potentiometer is spaced away from its respective electric resistive track when the container is spaced away from the dosing assembly, i.e. in a way where actually no wiper engages the resistive track.

In a thin film potentiometer configuration, when a container is inserted either partially or fully into the dosing assembly, a protrusion on the container may function as said wiper by co-acting with one of the layers of the thin film potentiometer.

In other embodiments, at least one of the protrusions of the container is made electrically conductive to engage and electrically connect with a corresponding electric resistive track disposed in the dosing assembly. In such embodiments, the dosing assembly is adapted to make electrical contact between the electric circuitry of the dosing assembly and a contact element disposed on the container, the contact element being electrically wired with the associated protrusion. An electric contact element and an electric conductive protrusion may be provided by injection moulding a container housing having an electric conductive element disposed in or on the housing section of the container. In such a container, electric conductive plastics together with non-conductive plastics may be used for co-molding the container. The contact element which is wired to said electrical conductive protrusion may be chosen to be disposed on one of the other coding protrusions, or alternatively, to one or more male or female fastening members defined on the container.

The dosing assembly defines a second fastening means which during fastening of the container to the dosing assembly engages a first fastening means of the container. Preferably, the first fastening means of the container are releasably coupleable to the second fastening means of the dosing assembly. In one embodiment a proximal facing surface of the second fastening means of the dosing assembly engages a distal facing surface of the first fastening means of the container.

In one embodiment, the container first fastening means are configured to be secured to the second fastening means of the dosing assembly by a sequence of movements comprising a relative axial movement along a first axis followed by a relative rotational movement around the first axis.

Also, the coupling scheme for coupling the container to the dosing assembly may comprise a concurrent axial and rotational movement, such as a helical movement. The rotational movement incurred by the concurrent axial and rotational movement is less than one revolution, such as less than 120 degrees, such as less than 90 degrees, such as less than 60 degrees, such as less than 30 degrees, such as less than 20 degrees. When the proximal facing surface of the first fastening means and the distal facing surface of the second fastening means are brought into engagement, rotation of the container relative to the dosing assembly may cause the container and the dosing assembly to be pulled towards each other.

The fastening means of the dosing assembly and the container may be adapted to provide a well defined stop ensuring that the container is fixedly located in a desired orientation with respect to the dosing assembly when the container is properly secured.

In one embodiment the second fastening means of the dosing assembly defines a groove adapted to receive a projection or male member defined by the first fastening means of the container. During fastening of the container to the dosing assembly, a substantially proximal facing surface of the second fastening means of the dosing assembly engages a substantially distal facing surface of the container. The predetermined movement is defined by the shape of at least one of the engaging surfaces. In a further embodiment the first fastening means defines a plurality of projections such as two, three or four, and the second fastening means defines a corresponding plurality of grooves adapted to be engaged by the projections.

Also, some or all of the fastening projections or male members may be formed on the dosing assembly to engage corresponding groves formed in the container.

Alternatively, the coupling scheme for coupling the container to the dosing assembly may include a purely axial movement between the container and the dosing assembly in order to properly secure the container to the dosing assembly. In such a system, the container and the dosing assembly may comprise means for rotationally aligning the container with the dosing assembly in one or more distinct relative rotational positions.

The medical delivery system may be designed so that the first and the second fastening means are configured to allow the container to be secured to the dosing assembly in a single predefined rotational orientation with respect to the dosing assembly. Alternatively, the first and the second fastening means are configured to allow the container to be secured to the dosing assembly in two predefined rotational orientations with respect to the dosing assembly where the two rotational orientations are opposed by 180 degrees. Still other embodiments include three or four distinct rotational alignments between the container and the dosing assembly.

The electric circuitry of the dosing assembly preferably includes a processor for monitoring the signals received by the electrical resistive tracks and contact switches contained in the dosing assembly.

In accordance with the particular design of the medical delivery system, the controller can be configured to provide an identification of the particular type of container mounted on the dosing assembly, thereby to obtain a simple logging into appropriate storage means along with information relating to the administrations performed. Further, the electric circuitry may include signalling means and be adapted to indicate to the user the particular kind of container mounted to the dosing assembly, i.e. by visual, auditive or tactile means.

In particular, the dosing assembly may be adapted to submit an alarm if the container mounted on the dosing assembly is deemed unacceptable by the dosing assembly, i.e. as being programmed into the controller. Also, the dosing assembly may be configured to accept a range of distinct containers while rejecting other distinct containers.

The information relating to the recognition of a particular container secured to the dosing assembly may be signalled directly by the dosing assembly, such as on a display or by audible means, or alternatively, indirectly by another device configured for communication with the dosing assembly.

Also, the dosing assembly may be configured to emit an alarm, or to disable operation of the dosing assembly, if the potentiometer arrangement senses that the first switch element is tripped (indicating proper mounting of a container) while the one or more potentiometers indicate that no wiper is associated with the corresponding electrical resistive track. This provides a safeguard against coupling of a non-compatible container, or coupling of a faulty container where one or more of the respective protrusions inadvertently is missing.

According to one embodiment of the invention, each particular dosing assembly may be dedicated a particular type of container or a particular range of containers solely by appropriate programming of the controller of the dosing assembly. This obviates mechanical modification of the particular dosing assembly to dedicate use thereof to particular types of containers.

In a SECOND aspect, the present invention relates to a container suitable for use (adapted to be used) in a medical delivery system according to the first aspect of the invention.

In one embodiment, the container is adapted to contain a medicament in a reservoir and to contain a slideably arranged piston which is moveable along a first axis in a distal direction towards an outlet of the reservoir so as to reduce the volume of the reservoir and expel the medicament through the outlet. When containing a medicament in the reservoir, the medicament is being withheld at the outlet of the container by a piercable seal or by a valve arrangement adapted to establish selective fluid communication through the outlet. The container further has a proximal end having a cavity adapted to receive driving means of the dosing assembly. The proximal end may include a portion having a circular cross-section, wherein first and second protrusions are located along the periphery of the circular section of the container and extends in the proximal direction. Optionally, one or more additional protrusions are formed and arranged along the periphery. For at least one of said protrusions, the centre-to-centre spacing between said at least one protrusion and each of its neighboring protrusions are non-equidistant. The number of protrusions may be selected as 2, 3, 4, 5 or 6 or even more protrusions. In situations where the container peripheral section is provided with exactly two protrusions, the neighboring protrusions referred to above shall mean one and the same other protrusion.

In particular embodiments, protrusions are arranged in pairs, each pair consisting of a first protrusion and a second protrusion arranged 180 degrees opposed to the first protrusion.

In one embodiment, the container comprises first fastening means for securing the container to second fastening means of the dosing assembly, where the first fastening means comprises two radially extending male members. A container according to another embodiment may comprise one radially extending male member and one radially inwards directed female member, such as a track disposed in an external surface of the container. Still, a container may contain at least two female members defining the first fastening means.

In particular embodiments, the container protrusions have a peripheral width along the periphery of the circular section which corresponds to less than 45 degrees, such as less than 30 degrees, such as less than 20 degrees. In some embodiments the peripheral width are less than 5 mm, such as less than 3 mm such as less than 2 mm.

In one embodiment the container comprises a cartridge holder and a cartridge defining said reservoir. The first fastening means may be defined by or attached to the cartridge holder. Moreover, the protrusions may be defined by the cartridge holder. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder so as to resist tampering. Even if such a cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly.

Alternatively, the container may define a monolithic element, i.e. forming a single element where the wall sections of the container is in fluid contact with the medicament accommodated therein. Such a monolithic element may be formed as a molded article made of a synthetic resin such as Topas(®) or polypropylene. However, any material which is suitable for long-term storage of the specific medication to be accommodated in the container may be used.

In one embodiment, the first fastening means are associated with the proximal end of the container. In other embodiments, the first fastening means are associated at a position extending from the proximal end of the container by a given distance, such as midway between the proximal and distal ends or even closer to the distal end of the container. In still other embodiments, the first fastening means are associated with the distal end of the container.

In one embodiment, the one or more protrusions extends from the proximal end of the container in the proximal direction. In other embodiments, the one or more protrusions extends radially outwards from an outer cylindrical surface section of the container.

According to one embodiment of the invention, different coding variants may be obtained by varying the distribution of the mechanical features along a well-defined geometry. In particular embodiments, it is hereby ensured that a container of a first medical delivery system is coded such that it cannot be used in a dosing assembly of a second medical delivery system. At the same time, it may be ensured that the container of the second medical delivery system is coded such that it cannot be used in the dosing assembly of the first medical delivery system. Accordingly, the medical system according to the present invention improves user safety as only predetermined containers may be used in a specific dosing assembly. Thus, the dosing assembly may be designated to be used with a predetermined kind/type and/or concentration of a medicament and containers accommodating other concentrations or types of medicaments cannot be used by the dosing assembly.

It will be appreciated that the invention according to the second aspect may comprise any feature and/or element of the invention according to the first aspect. In particular the container of the second aspect may comprise any feature and/or element of the container according to the first aspect of the invention.

In a THIRD aspect the present invention relates to a dosing assembly suitable for use (adapted to be used) in a medical delivery system according to the first aspect of the invention.

It will be appreciated that the invention according to the third aspect may comprise any feature and/or element of the invention according to the first aspect. In particular the dosing assembly of the third aspect may comprise any feature and/or element of the dosing assembly according to the first aspect of the invention.

In the context of the present invention, the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen (™).

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber or reservoir of the container may be defined by one or more sidewalls of the container housing and the slideably arranged piston. In most embodiments at least a part of the container is ring-shaped and defines a cylindrical cavity in which the piston is received. The distal end of the container may comprise a seal for penetration by a cannula so as to allow a medicament contained in the chamber to be expelled through delivery means such as through a cannula or through a tubing. The distal end of the container may be adapted to be attached to a holder holding a cannula. As an example, the distal end of the container may comprise a thread adapted to cooperate with a corresponding thread of the holder so as to allow the holder to be screwed onto the container. Alternatively, the distal end of the container may be adapted to couple to an infusion set.

The outlet of the container may be adapted to cooperate with or be defined by a cannula, a needle, a needle hub or an infusion set, or any other fluid communicating conduit adapted to provide fluid access to a medicament accommodated in the container.

The driving means of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly. The piston rod may be adapted to transfer a driving force to the piston either directly or via other parts situated in the dosing assembly and/or in the container.

DETAILED DESCRIPTION OF THE INVENTION

The invention will now be described in further detail with reference to the drawings in which.

Figure 4:
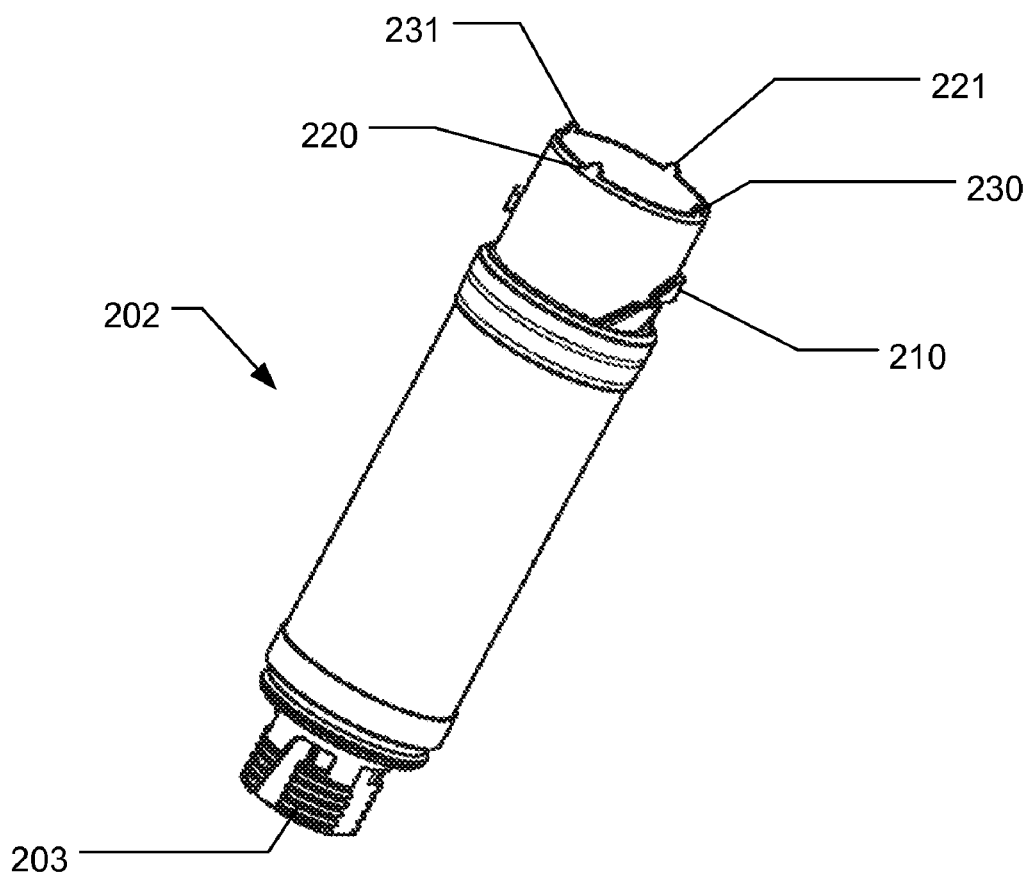
Figure 5:
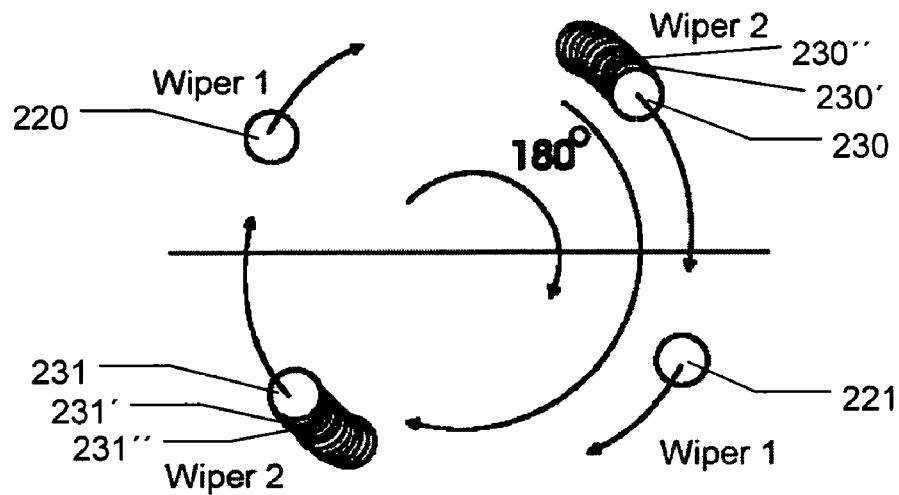
Figure 6:
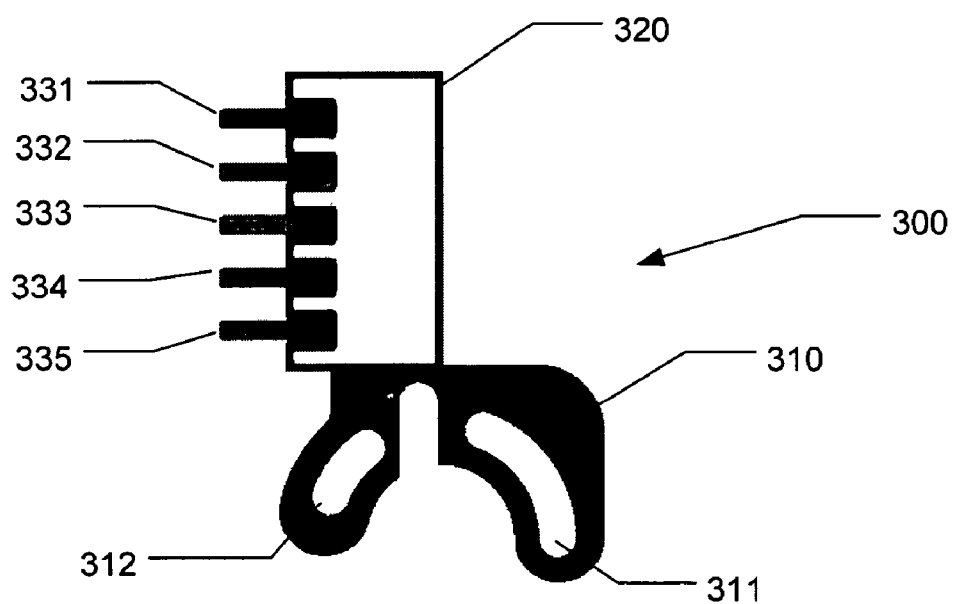
Figure 7:
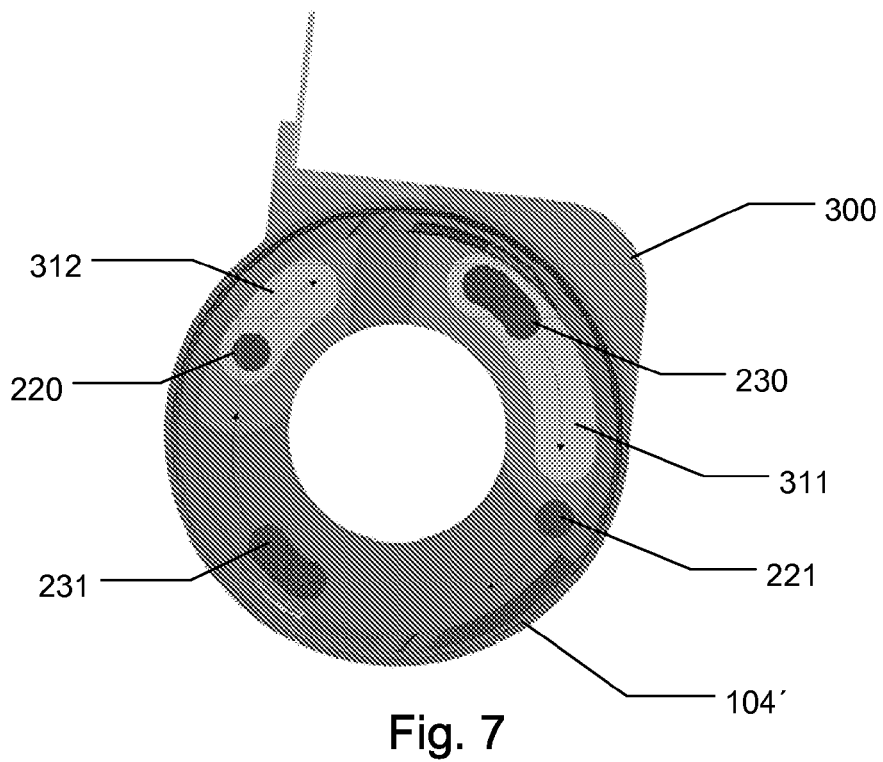
Figure 8:
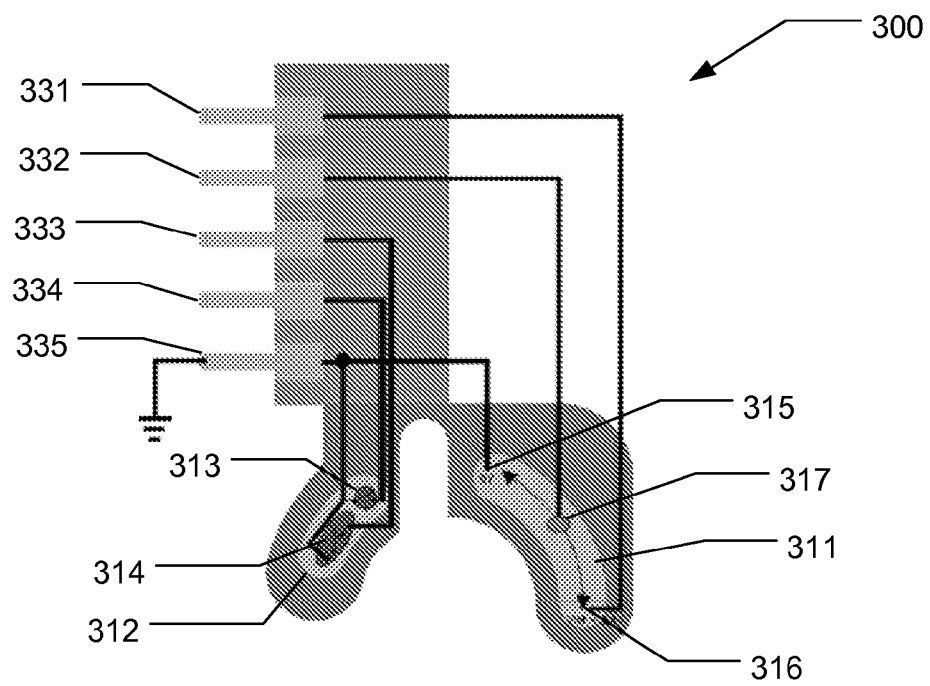

FIG. 4 shows a specific container forming part of the medical delivery system according to a first embodiment of the present invention, FIG. 5 is a schematic representation of the movements incurred by the protrusions of different types of containers during coupling of the different containers to a dosing assembly, FIG. 6 shows an embodiment of a sensor arrangement for inclusion into a dosing assembly, FIG. 7 is a schematic representation corresponding to FIG. 5 where the sensor arrangement of FIG. 6 has been inserted into a proximal part of a dosing assembly, FIG. 8 is a schematic view of electrical wirings of a sensor arrangement, FIGS. 9a, 9b and 9c depicts schematically a thin film potentiometer construction, FIG. 10 shows a further schematic representation of a thin film potentiometer adapted for inclusion in an embodiment of the present invention.

Figure 1:
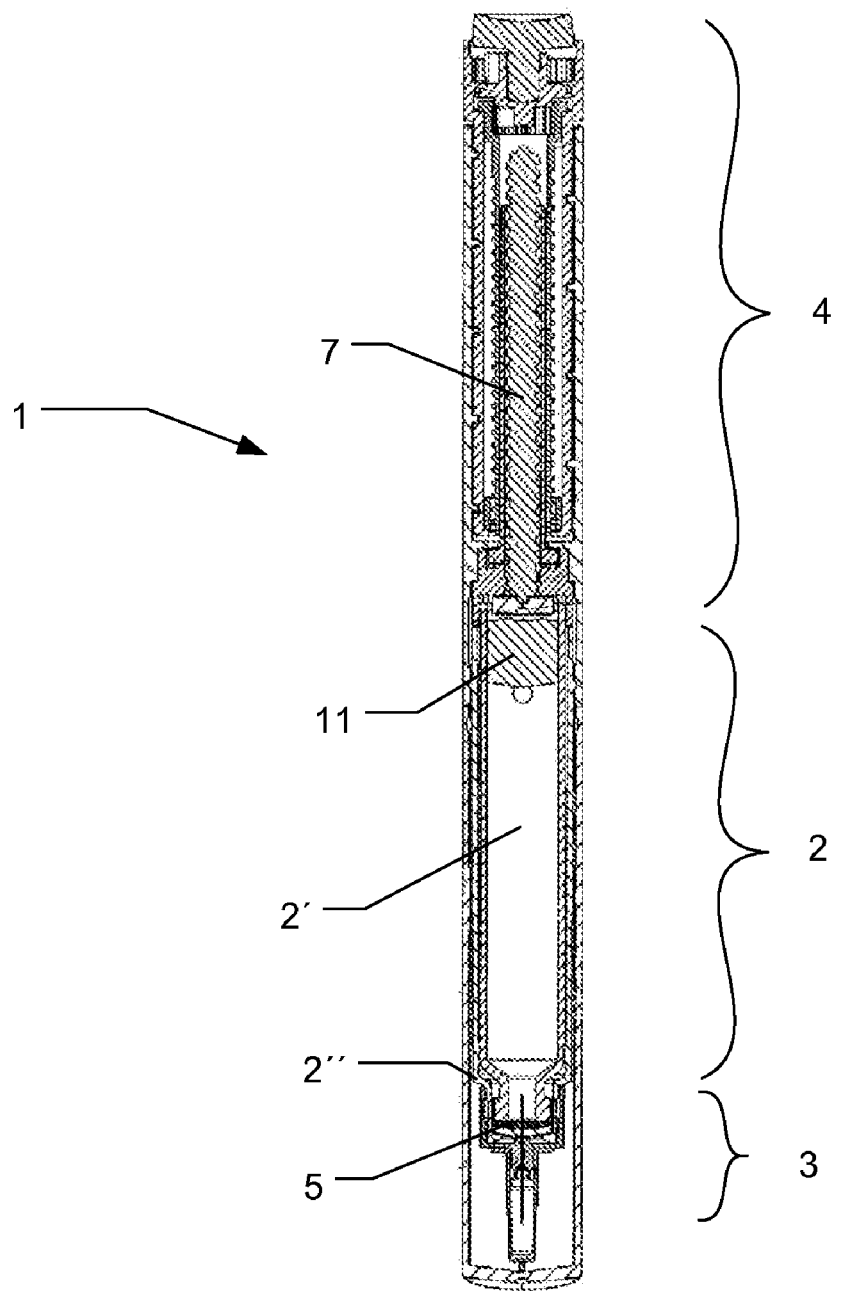
FIG. 1 shows a prior art medical delivery system.

FIG. 1 discloses a prior art medical delivery system forming an injection pen 1 comprising a medicament filled container part 2 which is adapted to be secured to a dosing assembly 4. In the depicted form, the dosing assembly 4 forms a mechanism for setting and injecting specific doses of a medicament from the container 2. The container 2 comprises an open distal part which is sealed by a piercable sealing member 5. The container further comprises a slideably mounted piston 11 which is adapted to slide towards the distal part of the container 2 when a force is exerted on the piston 11 in the distal direction. Typically, medication is delivered through a needle cannula 3 which may be releasably secured to the distal part of the container 2. When the container 2 is coupled to the dosing assembly 4, a force exerted by driving means 7 of the dosing assembly is transferred to the piston 11 whereby the medicament contained in the container 2 is expelled through needle 3.

In the depicted form, the container 2 is defined by a cartridge holder 2" adapted to receive a medicament containing cartridge 2', e.g. a standard glass cartridge. The container 2 is provided with fastening means (not shown) for fastening the container 2 to the dosing assembly 4 of the injection pen to form a releasable connection which then provides the possibility of reusing the dosing assembly with a new container after a previous empty container has been disposed off.

Figure 2:
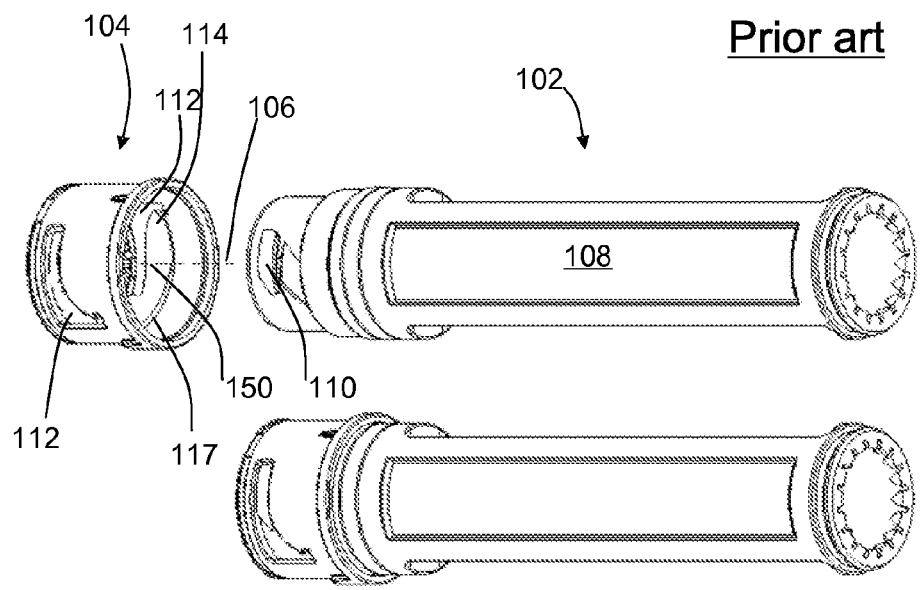
FIGS. 2 and 3 show a prior art container coupling system.
Figure 3:
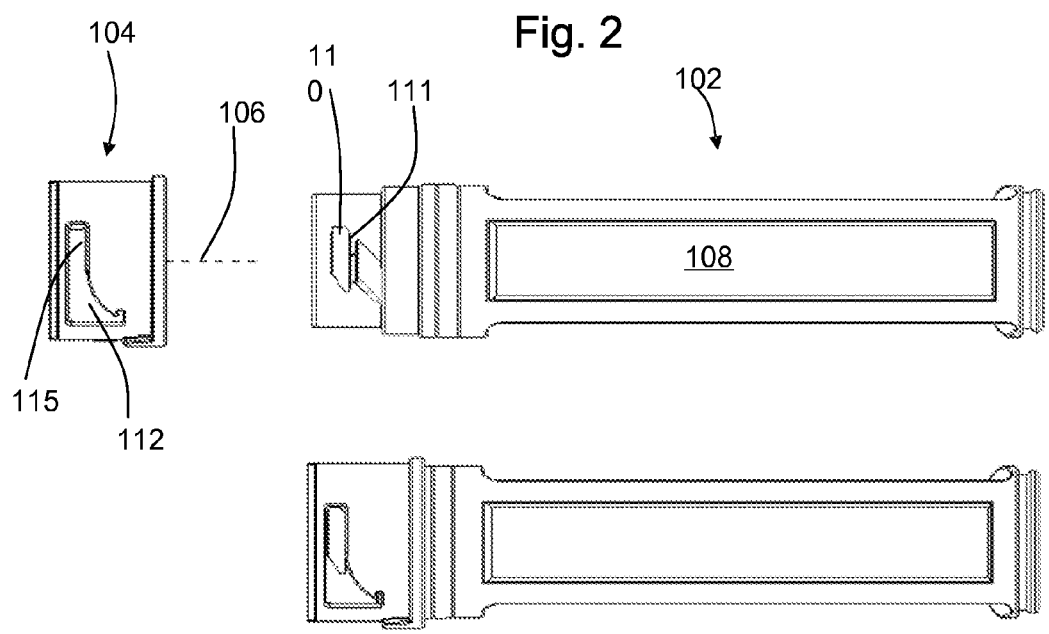

In accordance with the general delivery device concept outlined above, a recent state of the art syringe device has been marketed by the applicant as "NovoPen® 4". This device provides a durable dosing assembly which is adapted to accept disposable medication cartridges which can be easily exchanged by a user. The specific coupling mechanism for coupling a cartridge holder to the dosing assembly of the NovoPen® 4 offers a simple, intuitive and reliable coupling. FIGS. 2 and 3 shows detailed representations of selected parts of the NovoPen® 4 related to the coupling of the cartridge holder to the dosing assembly. The syringe device 100 of FIGS. 2 and 3 comprises a proximal part 104 and a distal part 102. In use, the proximal part 104 forms part of a dosing assembly which comprises driving means (not shown) for expelling minute quantities from syringe device 100. The driving means of the proximal part 104 comprises a piston rod (not shown) extending through a cartridge receiving cavity 150 of the proximal part 104 along a central axis 106. In use, the distal part 102 forms part of a container having a housing 102 for accommodating a reservoir such as a medicament cartridge (not shown). Further, the distal part 102 may be adapted to support or connect to a needle assembly (not shown) at the distal end of distal part 102.

The distal part 102 comprises two male members or projections 110 arranged on each side of the distal part 102. These projections 110 are used to secure the distal part 102 to the proximal part 104, by advancing the projections 110 into matching tracks forming grooves 112 of the proximal part 104. The grooves 112 are defined inside the cartridge receiving cavity 150 on an inner surface of the proximal part 104. The specific shape of each of the grooves 112 are defined by neighbouring ramp shaped ridges 114 protruding radially into the cartridge receiving cavity 150. Each of the grooves are defined by a first part having an opening for accepting axial entry of the distal part 102 by allowing the projections 110 to enter corresponding openings when the proximal part 104 and the distal part 102 are properly aligned. The opening of the grooves 112 are followed by slopes gradually transferring into grooves running along the inner peripheral direction, i.e. defined by a proximal facing surface 115. This arrangement provides a fastening movement between distal and proximal parts 102 and 104 comprising an initial relative axial movement, followed by a combined axial and rotational movement and ending in an exclusive rotational movement.

FIG. 4 show a first specific container forming part of the medical delivery system according to a first embodiment of the present invention. Here 202 denotes a medicament container adapted to contain a particular medicament and further adapted to be coupled to a dosing assembly (not shown). The dosing assembly may include a container receiving part 104' (see FIG. 7) arranged in the distal end of dosing assembly, the container receiving part 104' substantially corresponding to the proximal part 104 described above. The container receiving part 104' may comprise second fastening means defining one or more grooves for receiving corresponding male members or projections defining first fastening means 210 provided on the container 202. The grooves of the second fastening means defines an opening into which the male members of the first fastening means 210 can be inserted when the container 202 is properly aligned for axial entry into a container receiving cavity defined in the distal end of dosing assembly. The container 202 may be fastened to the dosing assembly by advancing the projection into its corresponding groove whereby a distal facing surface 211 of the projection (the first fastening means 210) engages a proximal facing surface of the groove (the second fastening means). Upon relative rotation between the dosing assembly and the container 202 the two elements are pulled towards each other due to the engagement between the distal facing surface 211 and the proximal facing surface of the second fastening means. Due to the angular extent of the groove the two elements can only be rotated a limited angle relative to each other i.e. less than one revolution.

In the embodiment shown, the number of distinct pairs of fastening elements on the container and on the dosing assembly are selected as two.

As in syringe device 100, the medical delivery system according to the first embodiment of the invention may be adapted for coupling container 202 to a dosing assembly by a fastening sequence comprising an initial relative exclusive axial movement, followed by a combined axial and rotational movement and ending in an exclusive rotational movement. As an alternative, the fastening sequence may comprise a relative axial movement followed by an exclusive rotational movement, i.e. forming a conventional bayonet coupling. Further embodiments may be designed so as to provide a purely axial movement in order to secure a container to the dosing assembly. In such a system, both the container and the dosing assembly are provided with means for ensuring rotational alignment between the container and the dosing assembly, wherein the alignment is selected as either one, two or three possible predefined positions.

As shown in FIG. 4, the container includes a circular peripheral section having a proximal end face provided with a number of protrusions 220, 221, 230, 231, each protrusion being arranged in a specific angular orientation with respect to the first fastening means 210. In the depicted embodiment, the protrusions 230 and 231 are positioned 180 degrees apart. Also the protrusions 220 and 221 are positioned 180 degrees apart. The centre-to-centre spacing between protrusion 230 and protrusion 221 is 80 degrees while the centre-to-centre spacing between protrusion 230 and protrusion 220 is 100 degrees.

The specific angular location of the protrusions 230 and/or 231 with respect to the fastening means is chosen to indicate a specific parameter of the container or the medicament contained in the container. According to the invention, additional distinct containers each having different types or kinds of medicaments contained therein differ from each other in that they have protrusions 230 and/or 231 located at mutually distinct positions with respect to the first fastening means so as to indicate the particular contents of each distinct container.

During the fastening sequence, the particular container is rotated with respect to the dosing assembly to secure the container to the dosing assembly. This is schematically depicted in FIG. 5, where the protrusions 220, 221, 230 and 231, during the locking movement, are rotated clockwise around a first axis which extends through the centre of container 202 in its longitudinal direction. The rotation required for locking container to the dosing assembly is in the depicted embodiment in the order of 20 to 40 degrees. However, other values of rotation may be used according to the specific design of the fastening mechanism.

Also depicted in FIG. 5 are protrusions 230' and 231' which represents a second distinct container and 230" and 231" which represents a third distinct container. Additional (non referenced) protrusions representing further distinct containers are also observable in FIG. 5.

FIG. 6 depicts a sensor arrangement 300 adapted to be mounted in the dosing assembly at the interface between the proximal end face of container 202 and a distal surface in the container receiving section of the dosing assembly, i.e. normal to the first axis. The sensor arrangement 300 includes an electric resistive track 311 and a switch configuration 312 having one or more switch elements disposed thereon. Electric resistive track 311 is adapted to engage wiper means which is configured to slide along resistive track 311 to thereby form a variable resistor. Both resistive track 311, wiper means and the one or more switch elements of the switch configuration 312 are via terminals 331-335 connectable to further electric circuitry including controller means adapted to both monitor the state of the electric resistive track 311 and the one or more electric switch elements of the switch configuration 312.

In this embodiment, the sensor arrangement 300 is formed as a thin film sensor assembly having a first sensor part 310 intended to be arranged normal to the first axis, and a second terminal part 320 arranged to be folded along the longitudinal axis of the dosing assembly, i.e. to be accommodated in the housing of the dosing assembly.

In FIG. 7, the sensor arrangement 300 has been assembled into the container receiving part 104'. In this figure, also the protrusions 220, 221, 230 and 231 are depicted in their initial position they obtain when the container 202 has been rotationally aligned and moved axially with respect to the dosing assembly. This situation corresponds to the state prior to the rotational locking movement is initiated.

As the container 202 is rotated clockwise relative to the container receiving part 104', in order to lock the container 202 to the dosing assembly, protrusion 230 slides along electric resistive track 311. Wiper means are configured for sliding along electric resistive track 311 in synchronization with the protrusion 230.

As the position of the wiper means corresponds to the position of the protrusion 230 with respect to the resistive track 311, the exact position of protrusion 230 with respect to the fastening means 210 on container 202 can be detected by monitoring an electric signal provided to the variable resistor.

In FIG. 8, the sensor arrangement 300 is schematically depicted along with lines representing the electrical wiring scheme of the sensor arrangement. As seen here, terminal 335 is wired to a first end 315 of the electric resistive track 311, terminal 331 is wired to the second end 316 of the electric resistive track 311, and terminal 332 is wired to the wiper means 317. Terminal 335 is electrically connected to a ground terminal of the electric circuitry and terminal 331 is connected to a supply voltage terminal of the electric circuitry. As the signal from wiper means 317 depends on the specific ratio of the electrical resistive track 311 disposed on each side of the wiper means 317, the position of the wiper means 317, and thus the corresponding position of the protrusion 230 can be monitored by the electric circuitry. In this configuration, the resistive track 311 and wiper means 317 forms a potentiometer assembly, e.g. a three terminal voltage divider. Thus, the voltage obtained at terminal 332 corresponds to the specific type of container being mounted on the dosing assembly as represented by the position of protrusion 230.

In FIGS. 7 and 8, an additional switch configuration 312 is shown having two contact switches 313 and 314 disposed thereon. Terminals 334 and 333 are connected to the switch elements 313 and 314 to facilitate reading of their state. Switch element 314 is adapted to provide a signal when a container initially is aligned with the dosing assembly and pressed axially against the dosing assembly. Thereby the switch element 314 provides a signal configurable for activating the electric circuitry which will start sampling the insertion of the container for container type recognition. Also, the switch element 313 may be provided which gives off a signal indicating that a container has been rotated fully clockwise against a well defined mechanical stop, thereby indicating that the container is properly secured against the dosing assembly. At this point, a reading of the potentiometer provides a distinct signal corresponding to the type of container which is secured to the dosing assembly.

The dosing assembly may be configured to obtain a first wiper reading when the switch element 314 is tripped. When the switch element 313 is tripped, indicating the proper securing of the container, a second wiper reading is obtained. In order to optimise system reliability, the first and second wiper readings may be compared taking into account the relative rotation performed during the rotational locking of the container.

All the depicted embodiments show a container and a dosing assembly being adapted for 180 degree symmetry, thereby providing a container which can be mounted in two mutually opposed angular orientations with respect to the dosing assembly. Thereby it is obtained, that a user is required only to provide a limited rotation of the container for securing the container to the dosing assembly, irrespective of the starting point of the mutual angular position of the two elements.

Accordingly, the protrusions 230 and 231 are provided with 180 degrees symmetry. Also, the protrusions 220 and 221 are provided with 180 degrees symmetry. This ensures that the container recognition can be properly carried out both when the container is secured in a first orientation and also in a second orientation which is oriented 180 degrees with respect to the first orientation.

FIGS. 9a, 9b, 9c and 10 schematically depict cross sectional views of a suitable thin film variable resistor 400 adapted for use as a potentiometer according to the embodiment shown in FIGS. 4-8. The thin film resistor 400 is formed as a first bottom layer 401 having a conductive resistive track disposed thereon and a second top layer 403 comprising a silver conductive layer having a low resistance. The top and the bottom layers are kept apart by a spacer layer 402 along the conductive resistive track, so that in the rest position, no galvanic contact is obtained between the two layers. When acted upon by a point-like contact member (such as a protrusion 230), which exerts an inward force on one of the two layers, the layers are locally brought into contact at the specific position of the point-like member. Thus, when a specific voltage is applied to each end 315, 316 of the conductive resistive track 311, and when the point-like contact member is pressed against one of the layers, the contact member and the co-acting layer acts as a wiper 317, facilitating a specific reading of a voltage level at the top layer wired to terminal 332. When the point-like contact member is removed, there is no voltage level applied on the top layer.

Also the switch elements 313 and 314 can be made from thin film technology, either as contact switch elements or as resistor switch elements.

The below part of FIG. 10 shows an electric diagram which corresponds to the electro-mechanical counterpart shown in the upper part of FIG. 10 with the wiper means 317 arranged midway between endpoints 315 and 316, where the electrical resistance R1 and R2 will be equal.

As indicated above, the sensor arrangement 300 is electrically connected to the electric circuitry which may comprise a controller, a supply voltage and means for communicating the signals obtainable from the sensor arrangement 300 or from the controller as applicable.

In order to gain additional reliability and redundancy of the container recognition, both voltage levels $V_{R1}$ and $V_{R2}$ can be sampled. The voltage over R1 plus R2 will always be $V_{ref}$. If broken glass or any other material acts as an additional wiper, $V_{R1}$ plus $V_{R2}$ is different from $V_{ref}$ and accordingly, an alarm or indication may be given.

Additionally, or as an alternative, the electrical current being drawn by the potentiometer can be monitored to reveal if an abnormal current is being drawn from the voltage supply, e.g. if the top layer has been forced into contact with the bottom layer along a distance which is longer than the contact length provided by protrusions 230 or 231.

In further embodiments, the dosing assembly may be provided with an additional potentiometer adapted to be mounted in the position to be wiped over by a second protrusion 231 (see FIG. 4), and the controller can be configured accordingly. Hereby, a redundant system can be obtained increasing the reliability of the recognition. For such a system, a 180 degree symmetry may be chosen for the pair of protrusions forming the potentiometer wipers and their respective electrical resistive tracks. However, relative orientations other than 180 degrees may be employed between the pairs of protrusions/resistive tracks.

In a further embodiment also comprising two potentiometers, the pair of protrusions forming wipers and their respective electrical resistive tracks are chosen so as to obtain a system having an increased number of distinct container codings as compared to a system having only one potentiometer. For such a system, each potentiometer delivers a detectable output according to the orientation of their respective wipers, and the controller is configured for detecting the particular combination of output signals from the two potentiometers for detecting the particular container secured to the dosing assembly. Different types of containers are represented by the two protrusions 230 and 231 and their mutual positions may be varied to obtain a large number of distinct codes.

In such a system the fastening means of the container and dosing assembly may be designed so as to exclusively allow the container to be secured to the dosing assembly at a single angular orientation with respect to the dosing assembly.

In accordance with the particular design of the medical delivery system, the controller is configured to provide an identification of the particular type of container mounted on the dosing assembly, thereby to obtain a simple logging into appropriate storage means of the type of container along with information relating to the administrations performed.

Alternatively, the electric circuitry is configured to indicate to the user the particular kind of container mounted to the dosing assembly, i.e. by visual, auditive or tactile means signalled by signal means of the electric circuitry.

In order to prevent mix-up of different container medicaments and non-matching or non-allowed dosing assemblies, two containers (202, 202') each having a specific distinct distribution of coding features, e.g. the position of the protrusions (230, 231) and (230', 231'), are dedicated specific coding features according to the medicament contained in each cartridge. Likewise, each distinct dosing assembly including container receiving sections (104, 104') are programmed for accepting or preventing usage of the containers provided with non-compatible coding features.

Some preferred embodiments have been shown in the foregoing, but it should be stressed that the invention is not limited to these, but may be embodied in other ways within the subject matter defined in the following claims. The figures e.g. discloses medical delivery systems of the present invention in the form of an injection pen, however, this particular delivery device and its shape is in no way limiting for the present invention as defined in the claims.

The invention claimed is:
1. A medical delivery system comprising:
a container adapted to contain a medicament in a reservoir and to contain a slideably arranged piston which is moveable along a first axis in a distal direction towards an outlet of the reservoir so as to reduce the volume of the reservoir and expel the medicament through the outlet, the container further comprising a first protrusion, the location of the first protrusion representing at least one parameter associated with the container,
a dosing assembly adapted to be secured to the container so as to allow driving means of the dosing assembly to move the piston of the container in the distal direction, the dosing assembly further having electric circuitry configured for identifying the location of the first protrusion on the container,
wherein the medical delivery system comprises a first electric resistive track disposed in the dosing assembly, and, in use, a first wiper slideably engaging said first electric resistive track, the first wiper being associated with said first protrusion when the container is secured to the dosing assembly, the first electric resistive track and the first wiper being coupled to the electric circuitry so as to detect the relative position of the first wiper with respect to the first electric resistive track to thereby identify said container.

2. A medical delivery system as defined in claim 1, wherein the dosing assembly comprises a first switch element which is adapted to cooperate with a second protrusion disposed on the container, the first switch element and the electric circuitry being adapted to detect when the container is correctly secured to the dosing assembly.

3. A medical delivery system as defined in claim 2, wherein the dosing assembly comprises a second switch element which is adapted to cooperate with said second protrusion disposed on the container, the second switch element being adapted to activate a controller of said electric circuitry responsive to initial coupling of the container to the dosing assembly.

4. A medical delivery system as defined in claim 1, wherein the medical delivery system comprises a second electric resistive track disposed in the dosing assembly, and a second wiper slideably engaging said second electric resistive track, and wherein the container comprises a third protrusion, the second wiper being associated with the third protrusion when the container is secured to the dosing assembly.

5. A medical delivery system as defined in claim 1, wherein the container has a proximal end adapted to be at least partly received in the dosing assembly and wherein at least one of said protrusions is/are arranged on the proximal end of the container extending in the proximal direction.

6. A medical delivery system as defined in claim 1, wherein the container has a generally cylindrical section and wherein at least one of the protrusions are arranged on the external face of the cylindrical section.

7. A medical delivery system as defined in claim 1, wherein the electric resistive track is a thin film potentiometer or a thick film potentiometer.

8. A medical delivery system as defined in claim 1, wherein at least one of said wipers are spaced away from its respective electric resistive track when the container is spaced away from the dosing assembly.

9. A medical delivery system as defined in claim 1, wherein the first and/or the third protrusion of the container functions as said wiper(s), when the container is secured in the dosing assembly.

10. A medical delivery system as defined in claim 1, wherein the container comprises first fastening means releasably coupleable to second fastening means of the dosing assembly by a sequence of movements comprising a relative axial movement along a first axis followed by a relative rotational movement around the first axis.

11. A medical delivery system as defined in claim 1, wherein the container comprises first fastening means releasably coupleable to second fastening means of the dosing assembly by a purely axial movement along the first axis and where the dosing assembly comprises means for rotational aligning the container with the dosing assembly.

12. A medical delivery system as defined in claim 10, wherein the first and the second fastening means are configured to allow the container to be secured to the dosing assembly in a single predefined rotational orientation with respect to the dosing assembly.

13. A medical delivery system as defined in claim 10, wherein the first and the second fastening means are configured to allow the container to be secured to the dosing assembly in two predefined rotational orientations with respect to the dosing assembly, the two rotational orientations being opposed by 180 degrees.

14. A container for use in the medical delivery system as defined in claim 2, the container being adapted to contain a medicament in a reservoir and to contain a slideably arranged piston which is moveable along a first axis in a distal direction towards an outlet of the reservoir so as to reduce the volume of the reservoir and expel the medicament through the outlet, the container further comprising a proximal end having a cavity adapted to receive driving means of the dosing assembly, the proximal end including a portion having a circular cross-section, wherein a first protrusion and one or more additional protrusions are located along the periphery of the circular section of the container and extends in the proximal direction, and wherein for at least one of said protrusions, the centre-to-centre spacing between said protrusion and each of its neighboring protrusions are non-equidistant.

15. A container as defined in claim 14, wherein the container comprises first fastening means for securing the container to second fastening means of the dosing assembly, the first fastening means comprising two radially extending male members.

16. A container as defined in claim 14, wherein the first protrusion and the one or more additional protrusions, during the locking movement, are rotated clockwise around the first axis for locking the container to the dosing assembly in the order of 20-40 degrees.

17. A medical delivery system as defined in claim 2, wherein the medical delivery system comprises a second electric resistive track disposed in the dosing assembly, and a second wiper slideably engaging said second electric resistive track, and wherein the container comprises a third protrusion, the second wiper being associated with the third protrusion when the container is secured to the dosing assembly.

18. A medical delivery system as defined in claim 2, wherein the container has a proximal end adapted to be at least partly received in the dosing assembly and wherein at least one of the first protrusion and the second protrusion is arranged on the proximal end of the container extending in the proximal direction.

19. A medical delivery system as defined in claim 4, wherein the container has a proximal end adapted to be at least partly received in the dosing assembly and wherein at least one of the first protrusion and the third protrusion is arranged on the proximal end of the container extending in the proximal direction.

20. A medical delivery system as defined in claim 5, wherein the container has a proximal end adapted to be at least partly received in the dosing assembly and wherein at least one of the first protrusion, the second protrusion and the third protrusion is arranged on the proximal end of the container extending in the proximal direction.

21. A medical delivery system as defined in claim 2, wherein the container has a generally cylindrical section and wherein at least one of the first protrusion and the second protrusion is arranged on the external face of the cylindrical section.

22. A medical delivery system as defined in claim 4, wherein the container has a generally cylindrical section and wherein at least one of the first protrusion and the third protrusion is arranged on the external face of the cylindrical section.

23. A medical delivery system as defined in claim 5, wherein the container has a generally cylindrical section and wherein at least one of the first protrusion, the second protrusion and the third protrusion is arranged on the external face of the cylindrical section.

24. A medical delivery system as defined in claim 4, wherein first protrusion of the container functions as said first wiper and the third protrusion of the container functions as said second wiper, when the container is secured in the dosing assembly.

25. A container as defined in claim 14, wherein at least one of the first protrusion, the second protrusion, and said additional protrusions extends less than 30 degrees along the periphery of the circular section.

26. A container as defined in claim 14, wherein at least one of the first protrusion, the second protrusion, and said additional protrusions extends less than 20 degrees along the periphery of the circular section.

* * * * *